(12) United States Patent
Tanaka

(10) Patent No.: US 6,537,798 B2
(45) Date of Patent: Mar. 25, 2003

(54) LIQUID FUEL-REFORMING PROCESS

(75) Inventor: Hideaki Tanaka, Osaka-fu (JP)

(73) Assignee: Masao Okada (JP)

( * ) Notice: Subject to any disclaimer, the term of this patent is extended or adjusted under 35 U.S.C. 154(b) by 0 days.

(21) Appl. No.: 09/793,571

(22) Filed: Feb. 27, 2001

(65) Prior Publication Data

US 2002/0155585 A1 Oct. 24, 2002

(51) Int. Cl.[7] .............................. C12P 1/02; C12N 1/14; C10G 32/00
(52) U.S. Cl. ..................... 435/281; 435/171; 435/254.3; 435/256.1; 435/913
(58) Field of Search ................................ 435/281, 171, 435/256.1, 254.3, 913

(56) References Cited

U.S. PATENT DOCUMENTS 4,113,444 A * 9/1978 Bunting et al. ................. 44/72
4,261,420 A * 4/1981 Hitzman ...................... 166/246

FOREIGN PATENT DOCUMENTS

JP 2000063851 * 2/2000

* cited by examiner

Primary Examiner—Herbert J. Lilling
(74) Attorney, Agent, or Firm—Jones, Tullar & Cooper, P.C.

(57) ABSTRACT

A process for reforming oil fuel comprises the steps of contacting oil fuel with activated aspergillus fungi for a certain period and then mixing the resulting oil fuel with unreformed oil fuel. The reformed oil fuel may be treated with a magnetic catalyst after treatment by the activated aspergillus fungi.

6 Claims, 3 Drawing Sheets

LIQUID FUEL-REFORMING PROCESS

BACKGROUND OF THE INVENTION

The present invention relates to a liquid fuel-reforming process and, more particularly, to a process for reforming oil fuels such as gasoline, diesel fuel, heavy oil and other liquid fuels, that is suitable for reconstruction of gas stations.

Recently, depletion of oil resources comes up as an important problem because of recent enormous amount of consumption of oil fuels. For this reason, measures for reduction of oil resources have been required. In addition, there are problems for immediate solutions including greenhouse reduction and so-called purification of pollution exhaust-gases such as carbon dioxide, nitrogen oxides (NOx), sulfur oxides (SOx), free-carbons, unburned hydrocarbons that result from consumption of mineral oil or imperfect combustion of mineral oils. In particular, the consumption of fuel oils is increased remarkably because of considerably increase in total number of automobiles, which in turn causes critical problems viewed in the light of health care. Thus, there is a great need for the solution.

The gas mileage of automobiles has been improved along with measures of the environmental pollution problem. The first approach for improvement in gas mileage was addition of a metal catalyst serving as an octane booster to gasoline. However, such a metal catalyst contains metal such as harmful lead or zinc, resulting in environmental pollution due to the harmful metal contained in the auto exhausts. Thus, the approach had fallen into disuse.

The next approach for improvement of imperfect combustion is to use radioactive ores such as monazite, uranium ore, and tourmaline containing rare earth element, or processed goods thereof as a catalyst for cracking of hydrocarbons in the fuel oil. The catalyst with the radioactivity of the legal standards (less than 4 microcuries) is employed in cracking of the oil fuel, the fuel mileage is improved only by 5 to 8%. This necessitates use of the catalyst with the radioactivity ranging from 40 to 250 microcuries since the cracking efficiency is increased along with an increasing radioactive level of the catalyst. If such a radioactive catalyst is put in a fuel tank of each automobile for a long period of time, there is a fear of radioactive leakage. In addition, the fuel in the tank may be contaminated with a small amount of the powdered radioactive catalyst and the exhausted gas may contain some amount of the powdered radioactive catalyst, resulting in environmental pollution. In particular, places where a large number of automobiles are concentrated, there is a fear of second pollution by radioactivity.

On the other hand, there is a great need for regeneration or reconstruction of closed gas stations along with an increasing number of closed gas stations.

SUMMARY OF THE INVENTION

It is therefore an object of the present invention to a oil fuel-reforming process that makes it possible to improve combustion-efficiency of internal-combustion engines used for automobiles, marines, airplanes, thermal power generators, boilers, burning appliances for heating systems, or the like and burning equipment, thereby reducing exhaust pollution gases such as free carbons, NOx, SOx and the like resulting from combustion of the oil fuels. The oil fuel used herein includes gasoline, light oil, heavy oil and other liquid fuels Another object of the present invention is to provide provide a process for reforming oil fuel that is suitable for regeneration or reconstruction of gas stations.

According to the present invention, these and other objects are achieved by providing a process for reforming oil fuel suitable for reconstruction of gas stations, comprising the steps of contacting oil fuel with activated aspergillus fungi for a certain period of time.

In a preferred embodiment, the contact between the oil fuel and the activated aspergillus fungi is carried out by supplying the fuel from a fuel tank to a cultivating tank including activated aspergillus fungi and then circulating it in the cultivating tank. Preferably, the reformed oil fuel is blended with unreformed oil fuel in a fuel tank so that the activated aspergillus fungi contained in the reformed oil fuel sustains cultivation in the fuel tank. In another preferred embodiment, the oil fuel is brought into contact with a magnetic catalyst after treatment by the activated aspergillus fungi.

In a preferred embodiment, the oil fuel is added with a certain amount of organometallic compound after treatment by the activated aspergillus fungi. Preferably, the organometallic compound is one or more chelate compounds including at least one of metals selected from the group consisting of copper, silver, platinum and palladium.

Further scope of applicability of the present invention will become apparent form the detailed description given hereinafter. However, it should be understood that the detailed description and specific example, while indicating preferred embodiments of the invention, are given by way of illustration only since various changes and modifications within the spirit an scope of the invention will become apparent to those skilled in the art from the detailed description.

BRIEF DESCRIPTION OF THE DRAWINGS

The present invention will become more fully understood from the detailed description given below and the accompanying drawings which are given by way of illustration only, and thus are not limitative of the present invention, and wherein:

Referring now to FIG. 1, there is illustrated a liquid fuel-reforming system embodying the present invention, which comprises a bacterial reforming tank (1), a catalytic reforming tank (10) and a storage tank (15).

Figure 1:
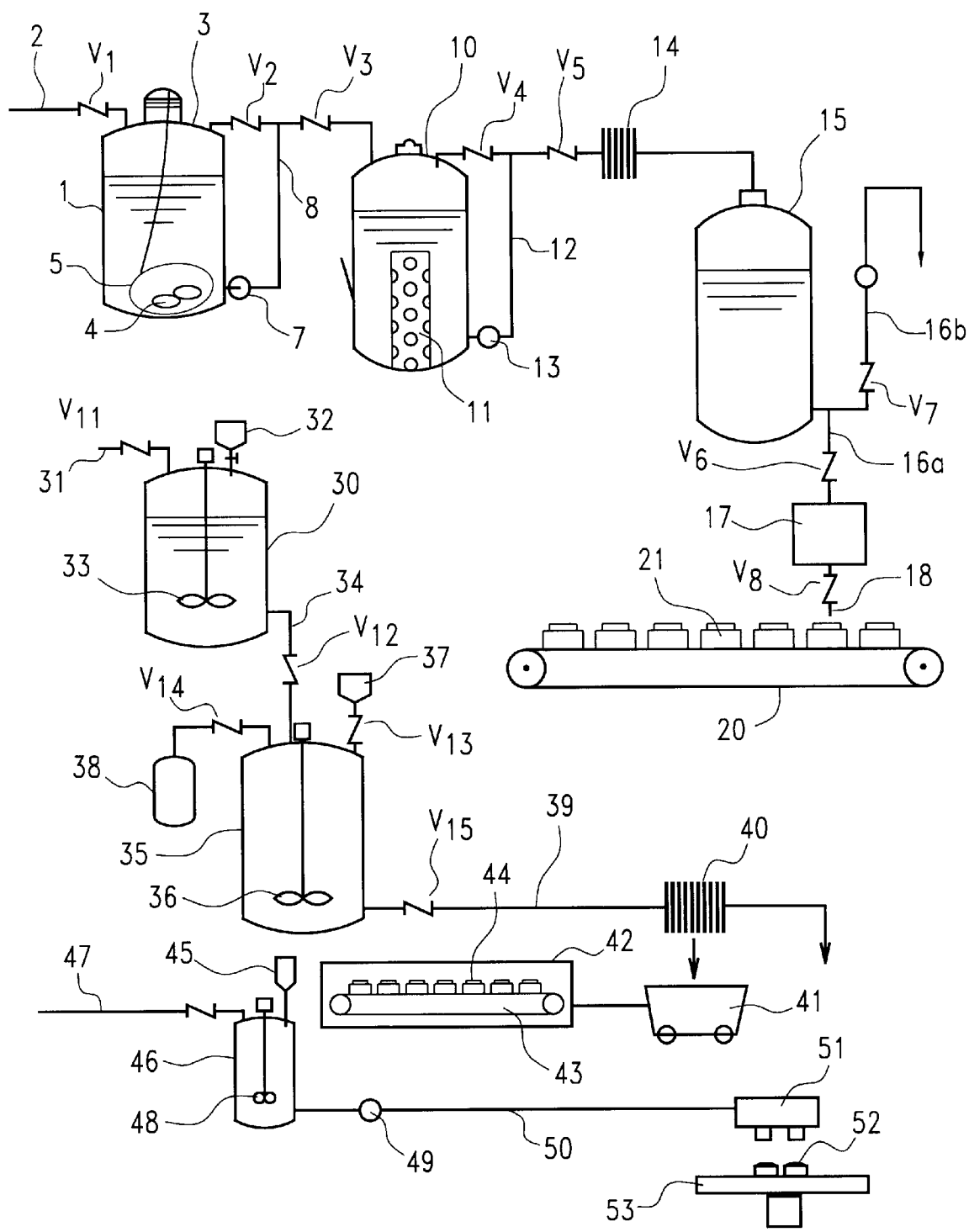
FIG. 1 is a schematic diagram illustrating a flow chart process of an oil fuel-reforming system embodying the present invention with a flow chart of a system for production of organometallic compound used therein.

The bacterial reforming tank (1) is provided at its top wall with a manhole (3) through which a cloth bag (5) including catalyst particles (4) is put into the tank (1). The tank (1) is connected to a fuel source via a fuel supply line (2) provided with a valve (V1) and connected to the top wall of the tank (1). The tank (1) is further provided with a circulating line (8) including a valve (V2) and a pump (7). The circulating line (8) is connected at its one end to a lower side of the tank (1) and at the other end to the top wall of the tank (1). The circulating line (8) has a branched supply line (9), which is provided with a valve (V3) and connected to the catalytic reforming tank (10) at a top portion thereof.

The bacterial catalyst (4) is composed of granular zeolite or apatite and contains activated aspergillus fungi of, for example, two hundred million (200000000) strains per gram. Before immersion in the oil fuel contained in the tank (1), the bacterial catalyst (4) is prepared by filling a bag (5) with granular zeolite or apatite containing resting aspergillus fungi and then immersing it into a nutrient solution for about 1 to 6 hours to activate the resting aspergillus fungi. The nutrient solution may be prepared, for example, by dissolving 100 parts by weight of glucose, 1 part by weight of potassium phosphate, 1 part by weight of urea, and 0.5 parts by weight of sodium chloride or sodium sulfate decahydrate in 1000 parts by weight of sterilized water.

The catalytic reforming tank (10) is provided with a perforated column (11), which is vertically mounted on a bottom of the tank (10) and filled with a magnetic catalyst containing 65% of ZrHfO2. The tank (10) is further provided with a circulating line (12) including a valve (V4) and a pump (13). The circulating line (12) is connected at its one end to a lower side of the tank (10) and at the other end to the top wall of the tank (10). The circulating line (12) is branched at its upper part to form a branched line (9), which is provided with a valve (V5) and connected to the storage tank (15) through a solid-liquid separator such as a filter press (14).

The storage tank (15) is provided with a line branched into two charging lines (16a, 16b) each having a valve (V6, V7). The charging line (16a) is connected to a charging device (17) by which the reformed fuel is packed into fuel cans (21) conveyed by a belt conveyer (20).

The system further includes a line for production of organometallic chelate compound catalyst, which comprises an autoclave (30), a reaction tank (36), a solid-liquid separator (40), a dryer (44), a solution tank (45) and a charging device (50). Arranged below the charging device (50) is a conveyer (53) for transportation of packed catalyst.

Using the above system, the method of the present invention is carried out in the following manner. The tank (1) is supplied with 2000 litters of an oil fuel through the fuel supply line 2. Then, the cloth bag (5) containing bacterial catalyst (4) is chained and put in the tank (1) through a manhole (3). The free end of a chain (6) connected to the bag (5) is anchored to the manhole (3) of the tank (1).

After the culture bag (5) was put on the bottom of the tank (1), the fuel in the tank is circulated by the circulating pump (7) through the circulating line (8) to bring the fuel into contact with the cultures. The pump (7) is operated at about 1-hour intervals to promote the dissolutive action of the aspergillus fungi. This operation is repeated for 1 week during which hydrocarbons with carbon atoms of 16 to 18 in the oil fuel are reformed to hydrocarbons with carbon atoms of 6 to 10 by the aspergillus fungi.

The reformed fuel is then supplied to the catalytic reforming tank (10) through the branched line (9) by the pump (7) as the valve V3 is opened while the valve V2 is closed. The reformed fuel in the tank (10) is circulated by the pump 13 through the circulating line (12) to bring it into contact with the magnetic catalyst containing 65% of ZrHfO2 contained in the perforated column (11). The hydrocarbons in the fuel are further reformed to lower hydrocarbons by the magnetic catalyst.

The resultant products are then supplied to the filter press (14) where the reformed fuel containing cultured aspergillus fungi is separated from solid contents in the product and supplied to the storage tank (15). The reformed fuel containing cultured aspergillus fungi is fed to the charging device (17) through the line (16a) and then charged into metal cans (21) on the conveyer (20). The charged metal cans (21) are then sealed and conveyed out of the system. In this case, if the reformed fuel is charged into the metal cans (21) so as to have an air layer between the top wall and the reformed fuel, the aspergillus fungi proliferate during transport or storage.

The reformed fuel containing cultured aspergillus fungi may be charged from the tank (15) into fuel tanks of individual automobiles via the branched line 16b.

Separate from the above, the organic metal chelate compound catalyst is produced in the following manner. Firstly, an alcohol solution is fed to the autoclave (30) through a line (31) and mixed with a mixture of acetylacetone and copper acetate (or silver acetate, platinum acetate, or palladium acetate or the like) by adding the mixture from a hopper (32) and stirring with an agitator (33).

The resultant metal acetylacetone chelate complex solution is added slowly to the reaction container (35) containing caustic soda and an alcohol solution previously introduced therein from a hopper (37) and a tank (38), to allow them to react with one another, the stirring is continued during reactions by an agitator (36). The reaction mixture is fed through a line 39 to the filter press (40) where solid bisacetylacetonatocopper(II) or other metal salt is separated from the mother liquor. The filter cake is put into a carrier (41), washed and separated by filtration to obtain past catalyst. The resultant past catalyst is put into a dryer (42) with trays (44) and then dried in the course of conveyance by enforcing ventilation The dried catalyst is then put into the tank (45) through a hopper (46) and dissolved in a mixed solvent of alcohol and hexane in the tank (46) by stirring with an agitator (48). An additional mixed solvent is introduced into the tank (45) through a line (47) to prepare a catalyst solution with a concentration of the catalyst ranging from 0.001 to 0.01%. The resultant catalyst solution is transferred to a filling device (51) through a line (50) by a pump (49), and then charged into small bottles (52) on a turntable (53). In use, the catalyst solution is added dropwise to the reformed fuel in the automobile fuel tank. The catalyst solution is generally added to the reformed fuel in an amount of 0.5 to 3 ml per 55 liters of the reformed fuel.

Figure 2:
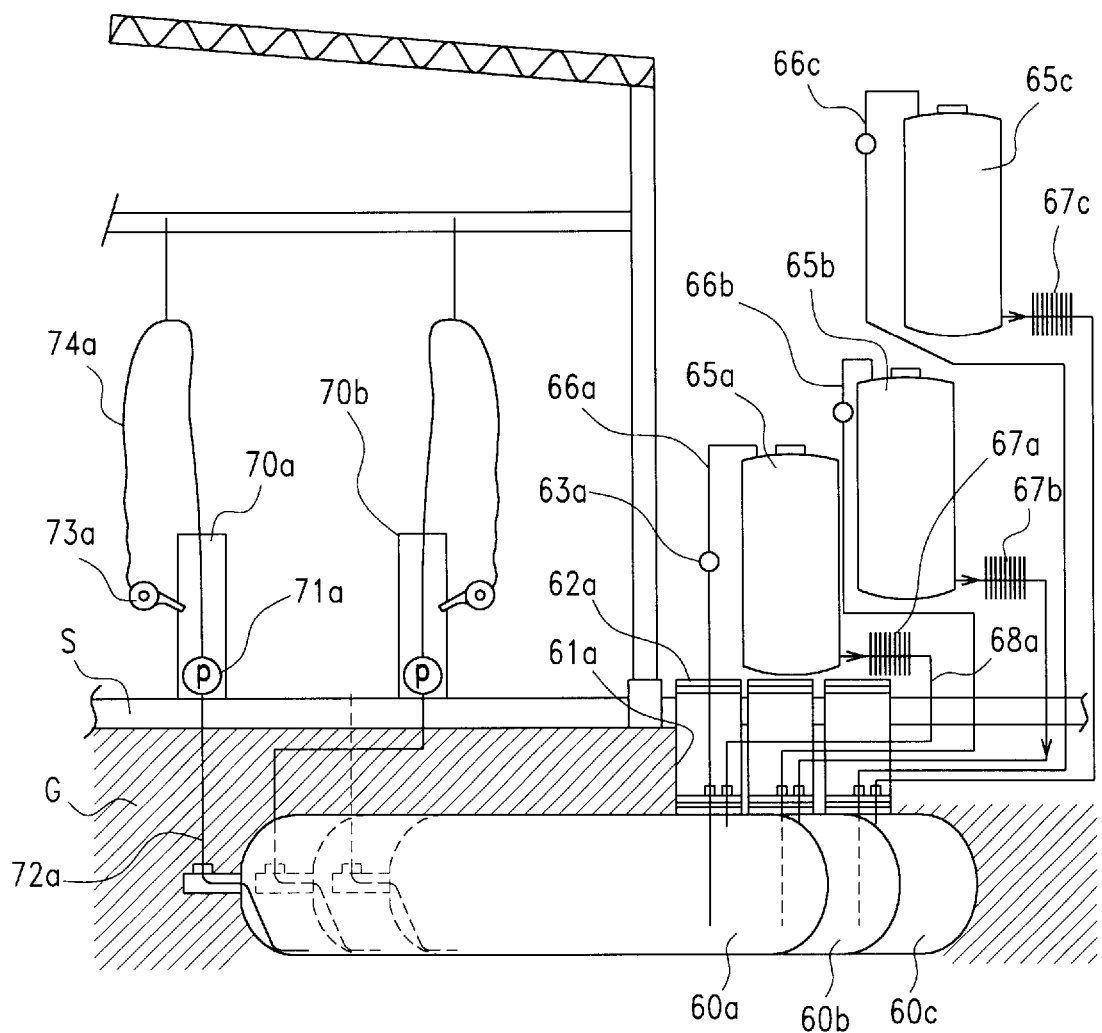
FIG. 2 is a side view illustrating one form of a filling station embodying the present invention.

Referring to FIG. 2 which illustrates a schematic side view of an oil station including three fuel-reforming systems for reforming different oil fuels such as gasoline, light oil or other fuel. Each reforming system includes a fuel tank 60a, 60b or 60c and a culture tank 65a, 65b or 65c connected to the corresponding fuel tank 60a, 60b, 60c. Each fuel tank 60a, 60b or 60c is connected to one or more oil feeders 70. All the fuel tanks 60a, 60b and 60c that have been wrapped with a piece of linen cloth and tarred with tar pitch to give corrosion resistance, are buried sideways in the ground G and covered with thick concrete S. The explanation will be made hereinafter on the fuel reforming system including the fuel tank 60a and the culture tank 65a since all the fuel-reforming systems have the same construction.

The fuel tank 60a is provided with an open-ended tube 61 extending upwardly from its barrel and closed by a stainless steel manhole cover 62 screwed on the open end. Between the open end of the tube 61 and the cover 62a there is provided a gasket to seal hermetically between them. The oil fuels such as gasoline, diesel fuel and other fuel are respectively charged into the corresponding fuel tanks 60a up to about 80% of the volume through the open-ended tube 61a.

The culture tank 65a is placed in an inside of a house (not shown), and connected to the fuel tank 60a through a fuel supply line 66a provided with a pump 63a. The supply line 66a is connected at its one end to the top of the culture tank 65a and at the other end to the fuel tank 60a. The other end of the supply line 66a passes through the cover 62a and terminates near the bottom portion of the fuel tank 60a. Further, the culture tank 65a is provided at its lower portion with an outlet line 67a connected to the top portion of the fuel tank 60a via a filter 68a. Within the culture tank 65a, plural cloth bags containing bacterial catalyst are suspended from the top of the culture tank 65a by a chain in the same manner as in the embodiment of FIG. 1.

The oiling device 70a is provided with a pump 71a connected to the fuel tank 60a via a line 72a. An output of the pump 71a is connected to an oil feeder 73a by a feeding line 74a.

In operation, bags of bacterial catalyst containing resting aspergillus fungi (200000000 stains per gram) were placed in the culture tank 65a after activating the resting aspergillus fungi contained therein. The activation was carried out by immersing the bags in a nutrient solution to activate contained in zeolite particles for 1 to 6 hours, and then dehydrated. The following is an example of a nutrient solution.

EXAMPLE 1

| Glucose | 100 parts by weight |
| Sterilized water | 1000 parts by weight |
| potassium phosphate | 1 part by weight |
| Urea | 1 part by weight |
| Sodium chloride (or sodium sulfate) | 0.5 parts by weight |

The oil fuel, e.g., gasoline (F) in the tank 60a is pumped up from the fuel tank 60a by the pump 63 and fed to the culture tank 65a through the line 66a where the oil fuel is brought into contact with the aspergillus fungi. The bacterial catalyst bags were replaced at interval of 6 months with new ones. Then, the oil fuel was supplied to the filter 67a to remove impurities and then returned to the fuel tank 60a through the line 68 to recirculate the system. The circulation of the fuel was continued for about 4 to 6 weeks. During circulation, the hydrocarbons having C16 to C18 in the oil fuel were biologically decomposed into lower hydrocarbons having C6 to C10. The resultant reformed oil fuel in the oil tanks 60a contains activated aspergillus fungi and thus the oil tanks 60a serves as an additional culture tank. The reformed fuel oil in the fuel tank 60a is fed to the oiling device 70a by the pump 71a and supplied to a fuel tank of an automobile by the oil feeder 73a through the feeding line 74a as occasion demands.

The gas mileages were determined for long-distance trucks that can carry a load of 10 tons using diesel fuels treated by the process of the present invention. The results are shown in FIG. 3.

Figure 3:
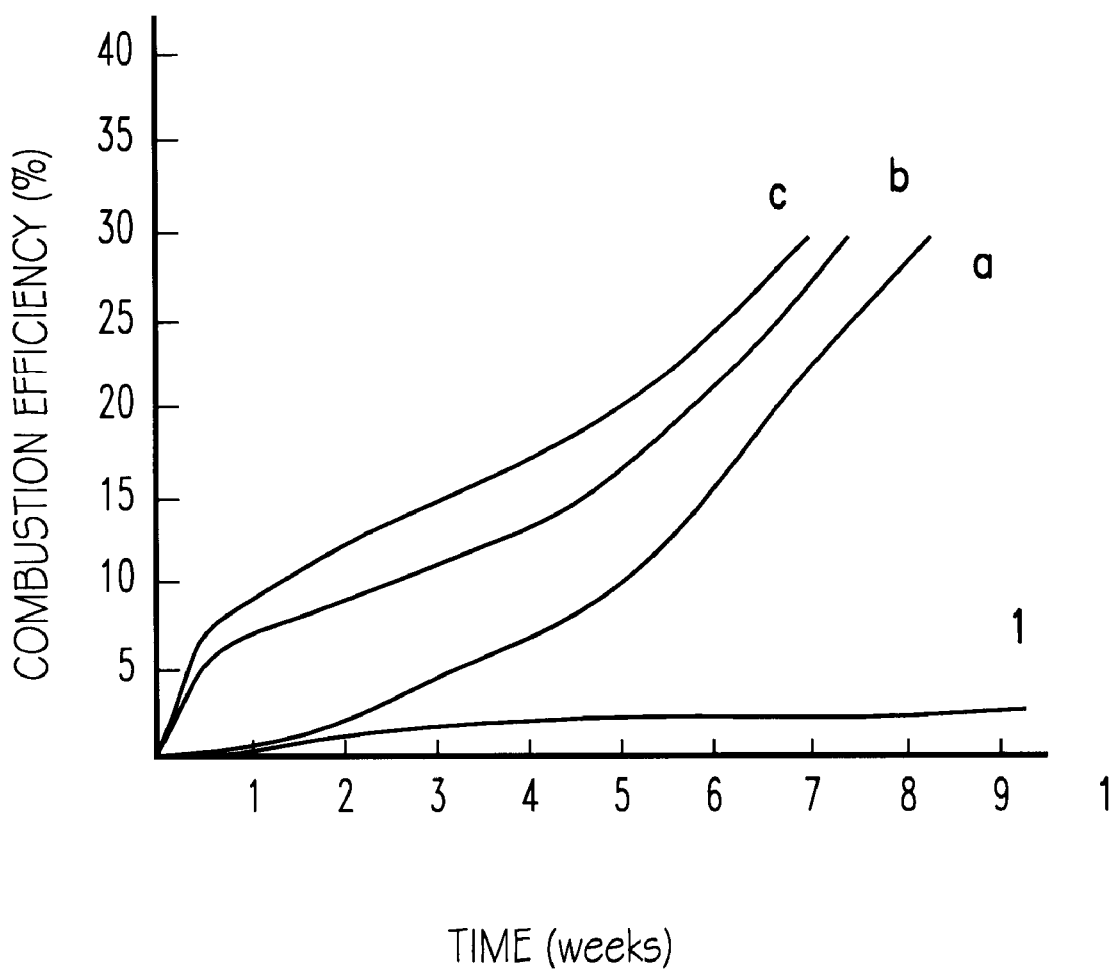
FIG. 3 is a graph illustrating a relation between combustion efficiency and treated time of liquid fuel.

FIG. 3 shows characteristic curves illustrating relationship between gas mileage and reforming time. A curve (a) shows the results for diesel fuel reformed only by aspergillus fungi. As the results of curve (a) show, the gas mileage is improved more than 30% by treatment of 5 weeks. A curve (b) shows the results for diesel fuel reformed by aspergillus fungi and added with 0.001% of bisacetylacetonatocopper (II). The organic copper chelate compound catalyst was prepared in the following manner. Firstly, one liter of acetylacetone was mixed with one liter of alcohol, and 10 g of copper acetate was dissolved in the resultant solution with stirring. The resultant solution was neutralized by adding an alkaline solution prepared by mixing 10% sodium hydroxide solution with 500 mol of alcohol, little by little, and then left to stand until the reaction products are precipitated. After filtering, the filter cake was purified by washing, dehydrated and then dried. The resultant bisacetylacetonatocopper(II) was dissolved in an alcohol-hexane mixture to prepare 0.001 to 0.01% solution of bisacetylacetonatocopper(II). By adding 1.1 to 3 ml of the resultant solution to 10 liter of diesel fuel, the gas mileage is much improved in a shorter period as indicated by the curve (b) in FIG. 3. This results from the fact the oil fuel is further improved in ignitionability by addition of copper compound and is ignited with ease even at lower temperatures. Thus, this reformed fuel is useful for wheeled vehicles used in cold districts. In addition, the copper compound is manufactured from copper acetate and acetylacetone as raw materials, so that there is no fear of increase in dioxins or NOx emitted from internal-combustion engine or burning appliances. This differs greatly from the copper compounds that have been manufactured from copper chloride or copper sulfate as the raw material.

A curve (c) in FIG. 3 shows the results for diesel fuel reformed by aspergillus fungi and a magnetic catalyst including ZrHfO2 and magnetic iron ore and added with 0.001% of bisacetylacetonatocopper(II). The magnetic catalyst was a mixture of 20 g of magnetic iron ore, 20 g of ZrHfO2 and 20 g of monazite. The diesel fuel was treated by immersing the magnetic catalyst in the diesel fuel for 1 hour after reforming by aspergillus fungi, and then added with 0.001% of bisacetylacetonatocopper(II). As can be seen from the curve (c), the gas mileage is improved by 35% and above.

Further, kerosene or lamp oil reformed by the present invention is improved in fuel economy about 10 to 15% and decreased in production of free carbon or peculiar smell to its own. In addition, the monazite catalyst including ZrHfO2 and tuff has a property to absorb NOx and SOx contained in the fuel, so that the fuel oil treated by the present invention makes it possible to reduce generation of air pollutants, as compared with the conventional oil fuel.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A process for reforming oil fuel, comprising the steps of contacting oil fuel with activated *Aspergillus fungi* obtainable by immersing *Aspergillus fungi* for about 1 to 6 hours in a nutrient solution consisting of 100 parts by weight of glucose, 1 part by weight of potassium phosphate, 1 part by weight of urea, and 0.5 parts by weight of sodium chloride or sodium sulfate decahydrate in 1000 parts by weight of sterilized water for a period effective to cause biological decomposition of $C_{16}$–$C_{18}$ hydrocarbon to $C_6$–$C_{10}$ hydrocarbon.

2. The process for reforming oil fuel according to claim 1, wherein said contact between the oil fuel and the activated *Aspergillus fungi* is carried out by supplying the fuel from a fuel tank to a cultivating tank including activated *Aspergillus fungi* and then circulating it in the cultivating tank.

3. The process for reforming oil fuel according to claim 1, wherein the oil fuel is brought into contact with a magnetic catalyst after treatment by the activated aspergillus fungi.

4. The process for reforming oil fuel according to claim 1, wherein the oil fuel is added with a certain amount of organometallic compound.

5. The process for reforming oil fuel according to claim 1, wherein the organometallic compound is a chelate compound including at least one of metals selected from the group consisting of copper, silver, platinum and palladium.

6. The process for reforming oil fuel according to claim 1, wherein the reformed oil fuel is blended with unreformed oil fuel in a fuel tank to culture the activated *Aspergillus fungi* in the fuel tank.

* * * * *